(12) United States Patent
Boisseau et al.

(10) Patent No.: US 9,901,751 B1
(45) Date of Patent: Feb. 27, 2018

(54) MULTI-LAYER RANGE MEASUREMENT APPARATUS FOR CHARACTERIZING CHARGED PARTICLE BEAMS

(71) Applicant: Pyramid Technical Consultants Inc., Lexington, MA (US)

(72) Inventors: Raymond P. Boisseau, Waltham, MA (US); John S. Gordon, Arlington, MA (US); Andrew Dart, Swampscott, MA (US); Julia C. Nett, Waltham, MA (US)

(73) Assignee: Pyramid Technical Consultants, Inc., Lexington, MA (US)

( * ) Notice: Subject to any disclaimer, the term of this patent is extended or adjusted under 35 U.S.C. 154(b) by 0 days.

(21) Appl. No.: 15/250,012

(22) Filed: Aug. 29, 2016

(51) Int. Cl.
| *A61N 5/10* | (2006.01) |
| *H05K 5/02* | (2006.01) |
| *H05K 5/00* | (2006.01) |
| *H05K 5/04* | (2006.01) |
| *H05K 9/00* | (2006.01) |
| *H01J 37/24* | (2006.01) |

(52) U.S. Cl.
CPC ......... *A61N 5/1075* (2013.01); *H01J 37/243* (2013.01); *H05K 5/0026* (2013.01); *H05K 5/0247* (2013.01); *H05K 5/04* (2013.01); *H05K 9/0049* (2013.01); *A61N 2005/1034* (2013.01); *A61N 2005/1087* (2013.01)

(58) Field of Classification Search
CPC ... A61N 5/1075; H01J 37/243; H05K 5/0026; H05K 5/0247; H05K 5/04; H05K 9/0049
See application file for complete search history.

(56) References Cited

U.S. PATENT DOCUMENTS

| 8,426,824 B2* | 4/2013 | Jongen | G01T 1/2935 250/370.01 |
| 2012/0310030 A1* | 12/2012 | Fontbonne | H01J 47/02 600/1 |
| 2014/0306119 A1* | 10/2014 | Hwang | H01J 37/3171 250/394 |
| 2015/0272669 A1* | 10/2015 | Brucker | A61B 18/1492 606/41 |

FOREIGN PATENT DOCUMENTS

JP 201318184 A * 9/2013

* cited by examiner

*Primary Examiner* — Marcus Taningco
(74) *Attorney, Agent, or Firm* — Intrinsic Law Corp.

(57) ABSTRACT

A multi-layer charged particle beam characterization system is disclosed, and method for using the same. A typical embodiment includes a plurality of two-sided metal plates, arranged as a stack, each metal plate having an electrical contact tab extending from at least one common edge of the metal plate, and a plurality of insulator films disposed between adjacent metal plates, each insulator film sized to match its corresponding metal plate. The tabs are coupled to a printed circuit board and connected to an external electrical connector to register a number of metal plates and insulator layers through which a charged particle beam has penetrated.

11 Claims, 12 Drawing Sheets

US 9,901,751 B1

MULTI-LAYER RANGE MEASUREMENT APPARATUS FOR CHARACTERIZING CHARGED PARTICLE BEAMS

TECHNICAL FIELD

The present application relates generally to the calibration and characterization of charged particle beams, such as charged particle pencil beams.

BACKGROUND

Beams of high-energy ions are commonly used in the field of medical radiation therapy. Use of proton beams in particular has become accepted for treatment of various types of cancer. The energy of the ion beam is an important parameter in radiation treatment, since it determines the depth of beam penetration. The depth of beam penetration is used by treatment planning systems to generate treatment plans for individual patients.

A calibration system is used to determine the depth of treatment of a beam as a function of the energy setting of the beam generator. Current calibration systems measure the depth of penetration of the beam in a water tank to simulate the beam penetration in a patient. An example of such a system is illustrated in FIG. 1A, which includes a beam generator and associated electromagnets 100, a water tank 110, an ion detection chamber 120, and a linear actuator 130. In operation, beam generator 100 generates a charged particle beam 140 (e.g., a charged particle pencil beam), which is directed to enter water tank 110. The beam 140 enters the tank 140 through an entry window 115 where it is detected by ion detection chamber 120, which is located at a variable distance or depth from the window 115. The ion detection chamber 120 measures the degree of ionization as a function of water depth, which is controlled by the linear actuator 130. The full curve of such a measurement as a function of water depth is referred to as the Bragg Curve. For a monochromatic proton beam, the Bragg Curve in pure water is well known, and is shown below for two representative initial proton energies (200 MeV and 250 MeV) in FIG. 1B.

Although water tank calibration is widely accepted, it can be prone to errors in operation and analysis and is not convenient to apply on a regular basis because of its size and weight. Alternative methods have been investigated, including the use of diode arrays to eliminate mechanical scanning. This technique suffers from low special resolution.

It would be desirable to have improved methods and systems for verifying the calibration of charged particle beams.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

In one aspect, the invention relates to an apparatus comprising an electrically-conductive housing; an entry window defined in the housing, the entry window comprised of a radiation-resistant polymer material, the entry window having an interior surface facing an interior of said housing and an exterior surface facing away from said housing; a conductive film disposed on said interior surface of said window and at least a portion of an interior surface of said housing proximal to said window, such that the conductive film and the housing in combination forms a continuous electrically-conductive shield; a plurality of metal plates disposed in said housing, each metal plate having an electrical contact tab extending from at least one common edge of said metal plate, each said metal plate having opposing first and second metal faces and a depth measured along an axis extending from said first metal face to said second metal face, said axis orthogonal to said first and second metal faces, each plate having a known composition, each plate oriented so that said first and second metal faces are parallel to said entry window; a plurality of insulator films disposed in said housing, each insulator film disposed between adjacent metal plates, each insulator sized to cover said first or said second face of said adjacent metal plates; and a printed circuit board disposed in said housing, said circuit board in electrical contact with a first subset of the electric contact tabs on said plurality of metal plates.

In another aspect, the invention relates to a kit comprising an apparatus and a non-transitory computer-readable medium. The apparatus comprises an electrically-conductive housing; an entry window defined in the housing, the entry window comprised of a radiation-resistant polymer material, the entry window having an interior surface facing an interior of said housing and an exterior surface facing away from said housing; a conductive film disposed on said interior surface of said window and at least a portion of an interior surface of said housing proximal to said window, such that the conductive film and the housing in combination forms a continuous electrically-conductive shield; a plurality of metal plates disposed in said housing, each metal plate having an electrical contact tab extending from at least one common edge of said metal plate, each said metal plate having opposing first and second metal faces, each plate having a known composition, each plate oriented so that said first and second metal faces are parallel to said entry window; a plurality of insulator films disposed in said housing, each insulator film disposed between adjacent metal plates, each insulator sized to cover said first or said second face of said adjacent metal plates; and a printed circuit board disposed in said housing, said circuit board in electrical contact with at a first subset of the electric contact tabs on said plurality of metal plates. The non-transitory computer-readable medium comprises data representing a position of each metal plate in said housing; a mass of each metal plate; and an area density of each metal plate.

In another aspect, the invention relates to a method of verifying a calibration of a charged particle beam generator. The method comprises calibrating said charged particle beam generator at a plurality of initial energy levels; after said calibrating, for at least some of said plurality of said initial energy levels, measuring a baseline current distribution generated by a charged particle beam that enters an apparatus comprising a plurality of metal plates and a plurality of insulator films, each insulator film interleaved between adjacent metal plates, each metal plate having substantially the same thickness and composition, said metal plates and insulator films disposed in an electrically conductive housing; with a computer comprising a microprocessor, generating baseline data comprising a baseline range and a baseline energy distribution of said charged particle beam for said at least some of said plurality of said initial energy levels, said baseline range and baseline energy distribution based at least in part on said baseline current distribution; after a first time interval, for said at least some of said plurality of said initial energy levels, measuring a verification current distribution generated by said charged particle beam that enters said apparatus; with said computer, generating verification data comprising a verification range and a verification energy distribution of said charged particle beam for said at least some of said plurality of said initial energy levels, said verification range and verification energy distribution based at least in part on said verification current distribution; with said computer, comparing said verification range and said verification energy distribution with said baseline range and said baseline energy distribution; and if said verification data is statistically different than said baseline data, re-calibrating said charged particle beam generator.

BRIEF DESCRIPTION OF THE DRAWINGS

For a fuller understanding of the nature and advantages of the present invention, reference is made to the following detailed description of preferred embodiments and in connection with the accompanying drawings, in which.

DETAILED DESCRIPTION

Figure 1A:
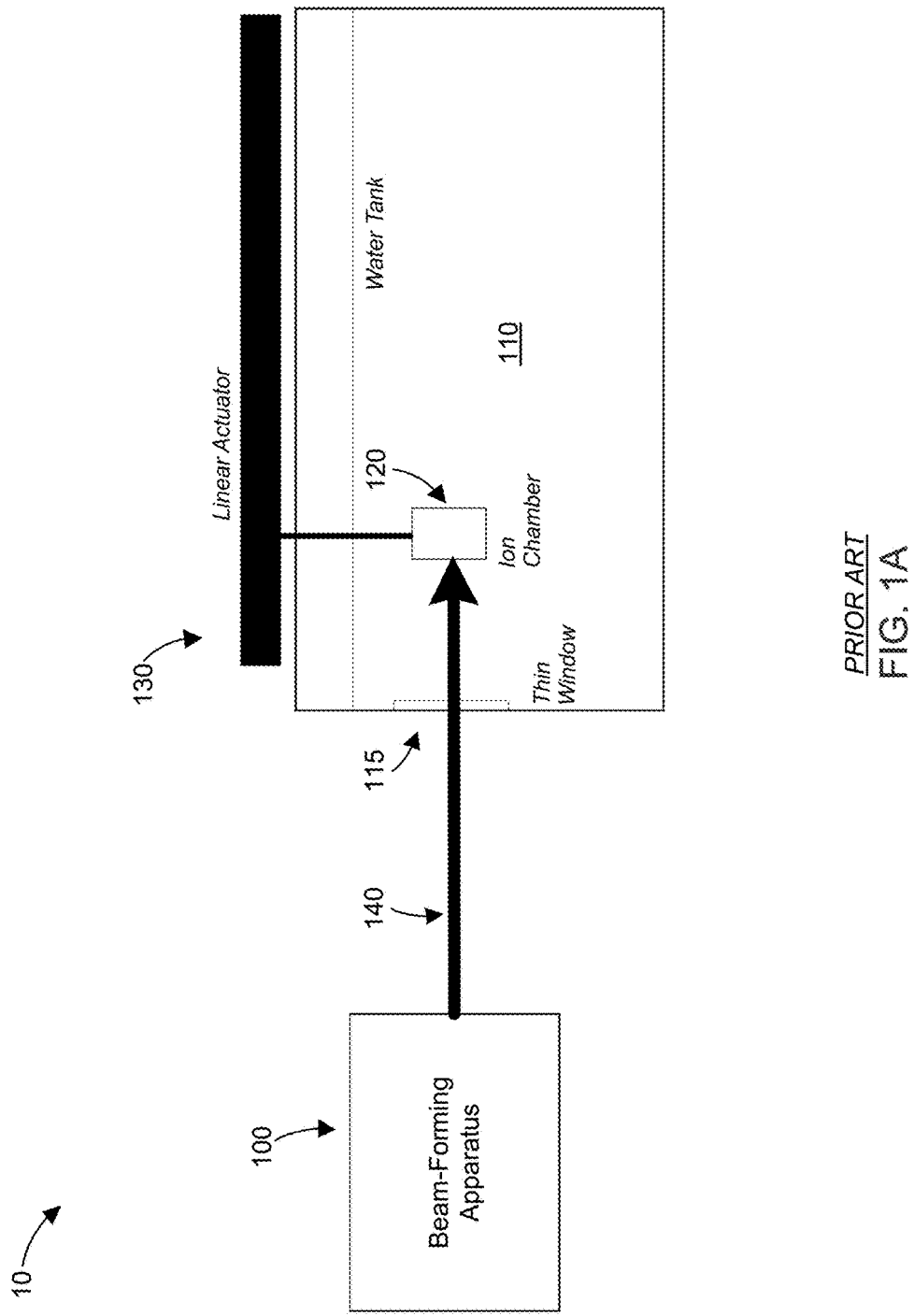
FIG. 1A illustrates an example of a water-tank calibration system according to the prior art.
Figure 1B:
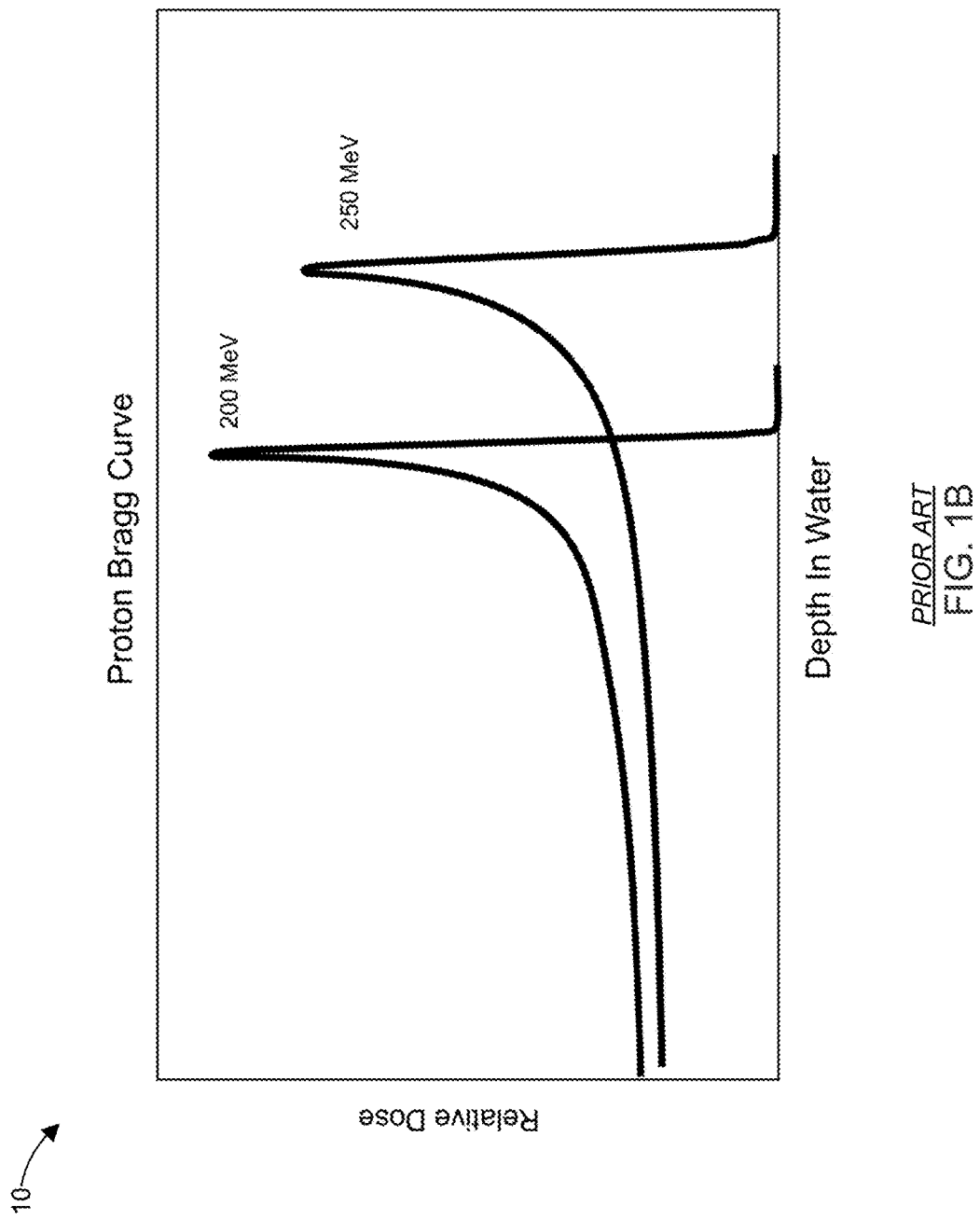
FIG. 1B illustrates a proton Bragg Curve in pure water for two representative initial proton energies, according to the prior art.
Figure 2:
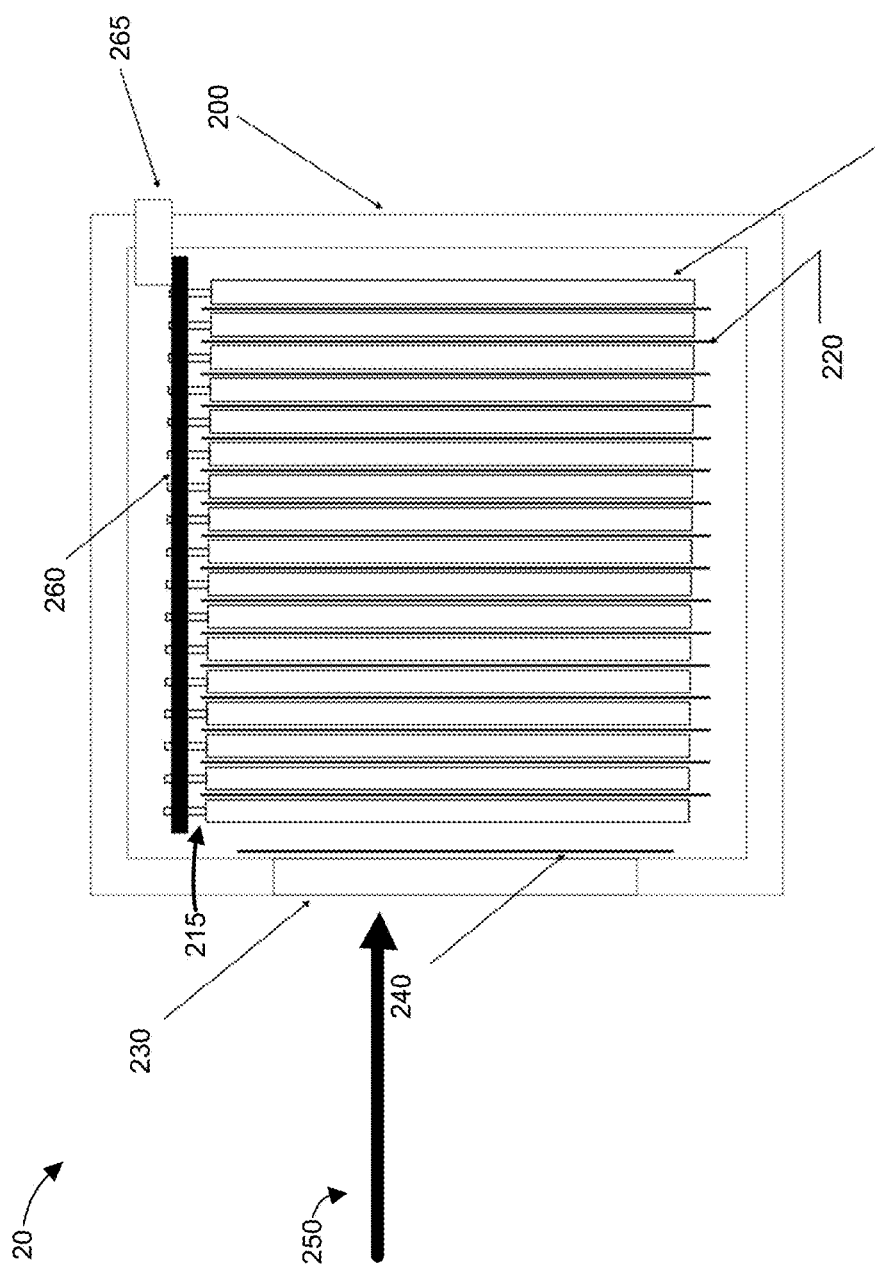
FIG. 2 is a top view of a multi-layer range verifier (MLRV) according to one or more embodiments.

FIG. 2 is a top view of a multi-level range verifier (MLRV) 20 according to one or more embodiments. The MLRV 20 includes a housing 200 that encloses a plurality of metal plates 210 and a plurality of insulation layers 220. The top of the housing 200 is not illustrated in FIG. 2 so the interior of housing 200 is visible. The housing 200 is electrically conductive and provides a continuous conductive surface to reduce or substantially eliminate external electromagnetic interference (EMI), similar to a Faraday cage. The housing 200 is formed out of a conductive material, such as a metal. For example, the housing 200 can be formed out of copper, brass, aluminum, or other conductive material. Our preferred housing material is aluminum which is light and easily machined, plated with nickel which is hard and non-oxidizing. The metal plates 210 may be constructed from any conductive metal, however, the preferred material is copper. Copper combines several useful properties for this application, including high density, good solderability, and ease of fabrication. A key advantage to copper is the fact that its activation products have a relatively short lifetime, which means that the device is safe to handle in minutes, and safe to transport in hours after use.

An entry window 230 is defined in the housing 200. The entry window 230 faces and receives an incident charged particle beam 250, such as a proton beam, which can be in the form of a pencil beam. To reduce energy attenuation to a value small compared to the low-energy limit of the device (about 100 MeV), the entry window 230 can be constructed out of an extremely thin radiation-resistant polymer, such as polyimide. In some embodiments, the window 230 has a thickness of about 10 to about 40 microns, about 20 microns to about 30 microns, about 25 microns, or any thickness or thickness range between any two of the foregoing values.

A conductive film 240 is disposed on the exterior surface of the entry window 230. By contacting the surrounding housing 200 directly or indirectly, the conductive film 240 completes the continuous conductive surface of the housing 200. In some embodiments, the conductive film 240 comprises nickel, gold, or a combination thereof. For example, the conductive film 240 can include a first layer of a first conductive material and a second layer of a second conductive material. As a specific example, the conductive film 240 can include a first layer of nickel and a second layer of gold. The first layer (e.g., the nickel layer) can be disposed on the interior surface of the entry window 230 (and surrounding housing 200) and the second layer (e.g., the gold layer) can be disposed on the first layer. Alternatively, the first layer can comprise gold and the second layer can comprise nickel. Each layer can have a thickness of less than or equal to about 200 nm, less than or equal to about 225 nm, less than or equal to about 250 nm, less than or equal to about 275 nm, less than or equal to about 300 nm, or any thickness or thickness range between any two of the foregoing values. The total thickness of the conductive film 240 can be less than or equal to about 400 nm, less than or equal to about 450 nm, less than or equal to about 500 nm, less than or equal to about 500 nm, less than or equal to about 600 nm thickness of the conductive film 240, or any thickness or thickness range between any two of the foregoing values. The thickness of the conductive film 240 is adequate for providing the shielding function (i.e., to shield external EMI), yet sufficiently thin to have a negligible impact on beam energy loss, and of sufficiently small mass as to have negligible effect on the activation products of housing 200. As used herein, "about" means plus or minus 50% of the relevant value. Alternatively, the conductive film 240 can be comprised of a single layer of material, such as nickel, gold or a combination, mixture, or alloy thereof. The conductive film 240 can be deposited through electroplating, sputtering, or other deposition technology. In a preferred configuration, conductive film 240 may be fabricated as part of the entry window 230.

The metal plates 210 are formed out of a conductive metal or metallic alloy of known composition. The known composition is relevant to compare the current distribution measured across the metal plates 210 in MLRV 20 with a theoretical model to determine the actual charge distribution and/or actual beam energy of the incident charged particle pencil beam 250. In some embodiments, the metal plates 210 are formed out of a pure or substantially pure conductive metal, such as copper, aluminum, silver, or gold. The purity level of the metal can be 99.9% or more pure so that the uncertainty in the composition does not contribute significantly to the overall device accuracy. Although alloys such as brass can be used as metal plates 210, in practice it can be difficult to know the precise composition of the alloy. In general, refining techniques can produce high purity material with far higher uniformity and composition accuracy than alloying techniques can produce high uniformity and well-known stoichiometry.

The metal plates 210 can have a square, rectangular, oval, circular, or other regular shape in a cross section orthogonal to the direction of travel of beam 150. Alternatively, they can have an irregular shape. In some embodiments, some or all of the metal plates 210 have a different cross-sectional shape. Regardless of the cross-sectional shape of the plate, the total surface area of each plate 210 is known as further discussed below. In addition, each metal plate 210 has a uniform or substantially uniform thickness. In some embodiments, the metal plates 210 have the same thickness and the same cross-sectional shape. In some embodiments, at least some of the metal plates 210 have different thicknesses and the same cross-sectional shape.

Each metal plate 210 optionally includes an electrical connection tab 215 that extends from an edge of the plate. The tab 215 is disposed in a corresponding slot in circuit board 260, which is then soldered to form an electrical connection. The tab 215 can be fabricated as part of the plate 210. In some embodiments, the tab 215 is plated with an oxidation-resistant material, such as tin, nickel, and/or gold before it is soldered to the circuit board 260. Alternatively, the metal plates 210 and circuit board 260 are electrically connected by spring-loaded contact pins, which can be disposed on the plates 210 and/or the circuit board 260. The spring-loaded contact pins can create corresponding electrical connections between the plates 210 and circuit board 260 without the use of solder, simply by bringing the circuit board 260 and plates 210 in physical and electrical contact through the spring action of the pins. The circuit board 260 includes a connector 265 for an input/output port that can be connected to an external device, such as a computer.

The insulation layers 220 are interleaved between adjacent metal plates 210. The material used to construct the insulation layers 220 can have high volume resistivity, preferably greater than $10^{12}$ Ohm-cm, so that the electrical resistance between plates is greater than $10^9$ Ohms. It should have the ability to withstand radiation doses of greater than $10^6$ Gray. Examples of insulator materials having these properties include polyimide (e.g., Kapton®), FR4 (circuit board material), and polyester (e.g., Mylar®). The insulation layers 220 can have a thickness of about 10 microns to about 100 microns, about 20 microns to about 80 microns, about 40 microns to about 60 microns, about 50 microns, about 12 microns, or any thickness or thickness range between any two of the foregoing values. The insulation layers 220 are sized to at least completely cover the exposed surfaces of the adjacent metal plates 210 to prevent electrical shorting. Thus, they can have the same or a larger cross-sectional shape as that of the adjacent metal plates 210. For example, FIG. 2 illustrates the insulation layers 220 as having a length (in the vertical direction) greater than the length of adjacent metal plates 210. Note that the contact tabs 215 do not require the insulation to extended to them, since the tabs are offset in the direction perpendicular to the beam axis to prevent electrical shorting.

Figure 3:
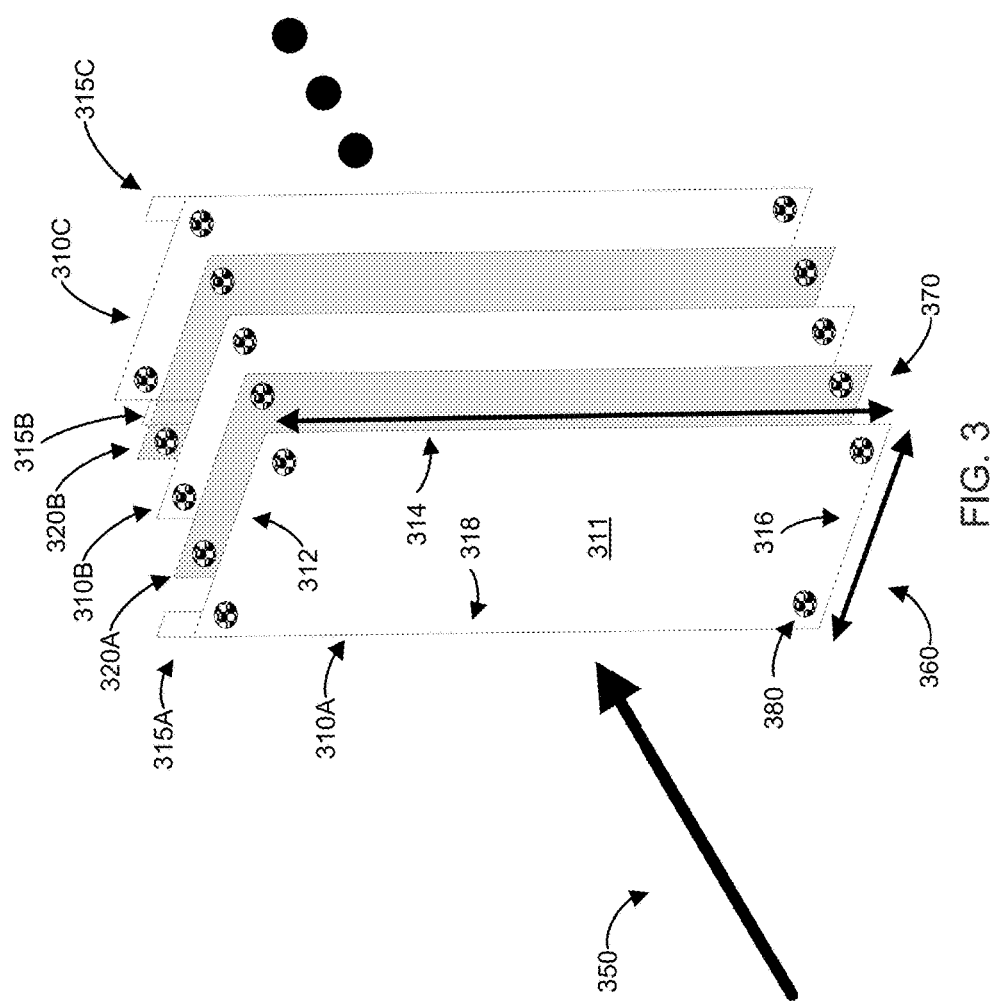
FIG. 3 is a perspective view of a plurality of interleaved plates and insulators of an MLRV according to one or more embodiments.

FIG. 3 is a perspective view of a plurality of interleaved plates 310A-C and insulators 320A-B of an MLRV according to one or more embodiments. The plates 310A-C (in general, plate(s) 310) and insulators 320A-B (in general, insulators 320) can be the same as the plates 210 and insulators 220 described above. Insulator 320A is disposed between plates 310A and 310B. Insulator 320B is disposed between plates 310B and 310C. The plates 310 and insulators 320 are positioned so that their respective faces are orthogonal to the direction of travel of pencil beam 350. The plates 310 and insulators 320 can include two or more alignment holes 380 through which alignment rods can be inserted to ensure proper alignment and positioning of the plates 310 and insulators 320. In some embodiments, four alignment holes 380 (as illustrated in FIG. 3) and four alignment rods can be used to provide improved mechanical stability and to facilitate a strong and uniform clamping force in the final assembly. The rods can be electrically insulating, mechanically strong, and have the ability to withstand radiation doses of greater than about $10^6$ Gray. For example, the alignment rods can be constructed out of FR4 (fiberglass composite often used in circuit boards) which has good mechanical stability and radiation resistance. In another example, the alignment rods can be constructed out of PEEK (Polyether ether ketone). In some embodiments, the alignment rods can be constructed out of two or more materials, such as FR4 and PEEK.

Each plate 310A-C includes a respective electrical connection tab 315A-C (in general, tab(s) 315), which can be the same as the tabs 215 described above. As illustrated, each tab 315 is disposed on a common edge 312 of each plate 310. In some embodiments, the tabs 315 can be disposed on two or more edges of the plates 310, such as on edge 312 and edge 314, 316, and/or 318. For example, plates 310A-C have tabs 315A-C disposed on their respective edge 212 (as illustrated) while plates 310D-F (not illustrated) can have tabs 315D-F (not illustrated) disposed on their respective edge 314. The tabs 315 are optionally offset laterally from one another along a width 360 or length 370 of each plate 310.

Prior to assembly into MLRV 20, the dimensions of each plate 310 are measured as precisely as practical, such as with an accuracy of about 0.001", to determine its total surface area. In addition to measuring the dimensions, the mass of each plate 310 is measured as precisely as possible prior to assembly. In some embodiments, the plates 310 are manufactured to be substantially identical in mass such that the plates 310 have less than about a 2% variation in mass from a mean or median mass of the plates 310, less than about a 1% variation in mass from the mean or median mass of the plates 310, less than about a 0.5% variation in mass from the mean or median mass of the plates 310, or any variation or range of variations between any two of the foregoing values. The plates 310 can be marked with a unique identifier so the characteristics of each plate and its location (plate number) are known in the assembled MLRV 20. This data is used to model the pencil beam 350 as described herein.

Likewise, the dimensions of each insulator 320 are measured as precisely as practical, such as with an accuracy of about 0.001", to determine its total surface area prior to assembly. In addition to measuring the dimensions, the mass of each plate 310 is measured as precisely as possible prior to assembly of MLRV 20. In some embodiments, the insulators 320 are manufactured to be substantially identical in mass such that the insulators 320 10 have less than about a 2% variation in mass from a mean or median mass of the insulators 320, less than about a 1% variation in mass from the mean or median mass of the insulators 320, less than about a 0.5% variation in mass from the mean or median mass of the insulators 320, or any variation or range of variations between any two of the foregoing values. The insulators 320 can be marked with a unique identifier so the characteristics of each plate and its location (plate number) are known in the assembled MLRV 20. This data is used to model the pencil beam 350 as described herein. The plates 310 and insulators 320 contribute similarly to the stopping of the beam as a function of their area density and mass.

Figure 4:
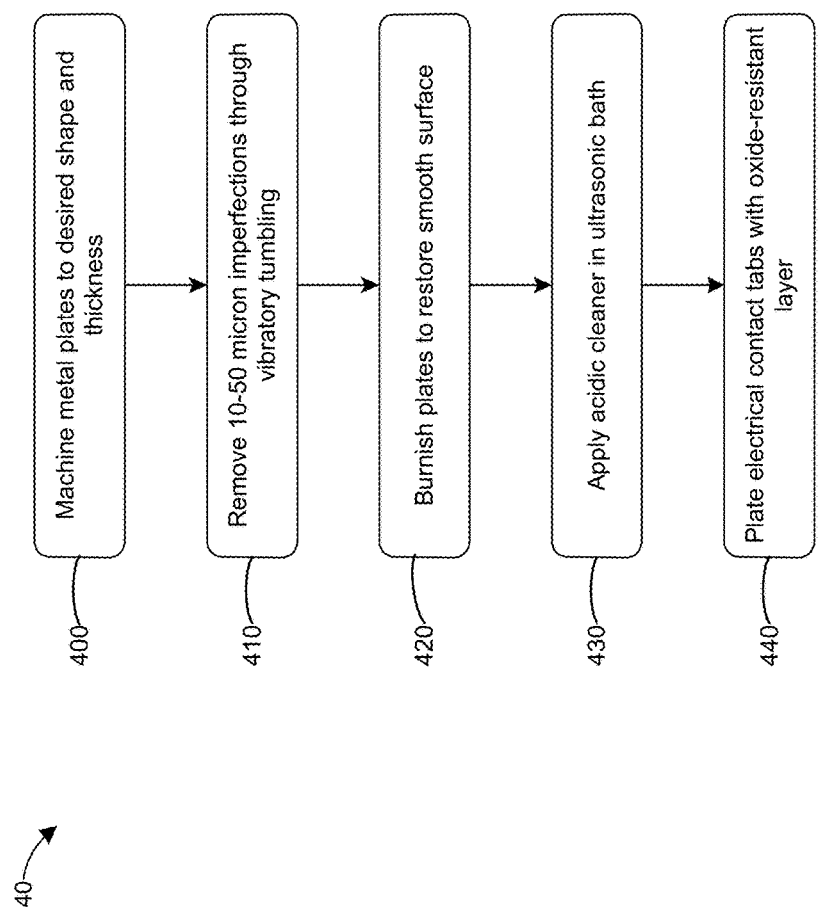
FIG. 4 is a flow chart of a method for processing metal plates to reduce signal error and/or distortion according to one or more embodiments.

FIG. 4 is a flow chart 40 of a method for processing metal plates to reduce signal error and/or distortion according to one or more embodiments. Since the currents measured by MLRV 10 are extremely small (e.g., less than 1 nanoAmpere), it is desirable to reduce any source of measurement error wherever possible.

One source of measurement error and/or distortion can occur from signal leakage or electrical shorting through insulator layer 120/220. For example, the small imperfections on the surface of the metal plates after machining can puncture the adjacent insulator film and cause an electrical short between adjacent metal plates. Another source of measurement error can occur as a result of a corona discharge around microscopic point imperfections on the plate. The corona discharge can be driven by a burden voltage of the readout electronics. The effect of a corona discharge is generally non-Ohmic and, thus, difficult to compensate in modeling.

Another source of measurement error and/or distortion can occur from the buildup of an oxide layer along the signal chain. Oxide layers can create high series resistance, which can combine with the inherent capacitance of the plates to create a low-pass filter. This effect can appear as channels having a slow response time. The effect of oxide buildup can impact the signal chain most noticeably at the electrical contact tabs, where the ratio of the exposed surface area (where oxide buildup can occur) to mass is the greatest.

In step 400, the metal plates are machined to a desired shape and thickness. As discussed above, each plate preferably has the same shape (e.g., rectangular) and thickness.

In step 410, the machined plates are placed in a vibratory tumbler with a lightweight plastic medium to substantially remove imperfections on the surface of the plates on the 10-50 micron scale. Examples of the imperfections that can be removed in step 410 include machining burrs, sharp edges, and other imperfections. Because the plates are delicate, low-mass tumbling media are required. These are readily available in the form of "plastic tumbling media." We select a shape of small cones to properly deburr the holes and edge burrs while having a smaller effect on the flat surfaces. This step typically runs for 1-2 hours.

In step 420, the plates are then burnished to restore a smooth surface on the 1-5 micron scale. This step uses "precision ceramic media" which is a hard ceramic in the form of small 1-6 mm diameter balls. These do not remove material at all, but simply burnish the surface. This step typically runs for 1-2 hours.

In step 430, the plates are immersed in an acidic cleaner (e.g., Alconox Citrojet®) in an ultrasonic bath to remove any oxide that built up on the plate surface after the burnishing step 420. Step 430 preferably occurs immediately after step 420, though this is not a requirement. Ultrasonic cleaning is in a 2.5 gallon laboratory unit with 160 W of sonic power at 40 kHz. This step is typically run for 10 minutes.

In step 440, an oxide-resistant layer, such as tin, is deposited on the electrical contact tabs. For example, the plates can be disposed in an immersion tin solution to deposit the tin layer on the electrical contact tabs. This layer can optionally be overcoated with electroplated or immersion gold. The oxide-resistant layer can also include nickel in some embodiments. The oxide-resistant layer protects the electrical contact tabs from oxide buildup until they are soldered to the circuit board.

Steps 410 and 420 can reduce the signal error and/or distortion caused by electrical shorting and corona discharge, discussed above. Steps 430 and 440 can reduce the signal error and/or distortion caused by the buildup of an oxide layer on the plates, as discussed above.

Figure 5:
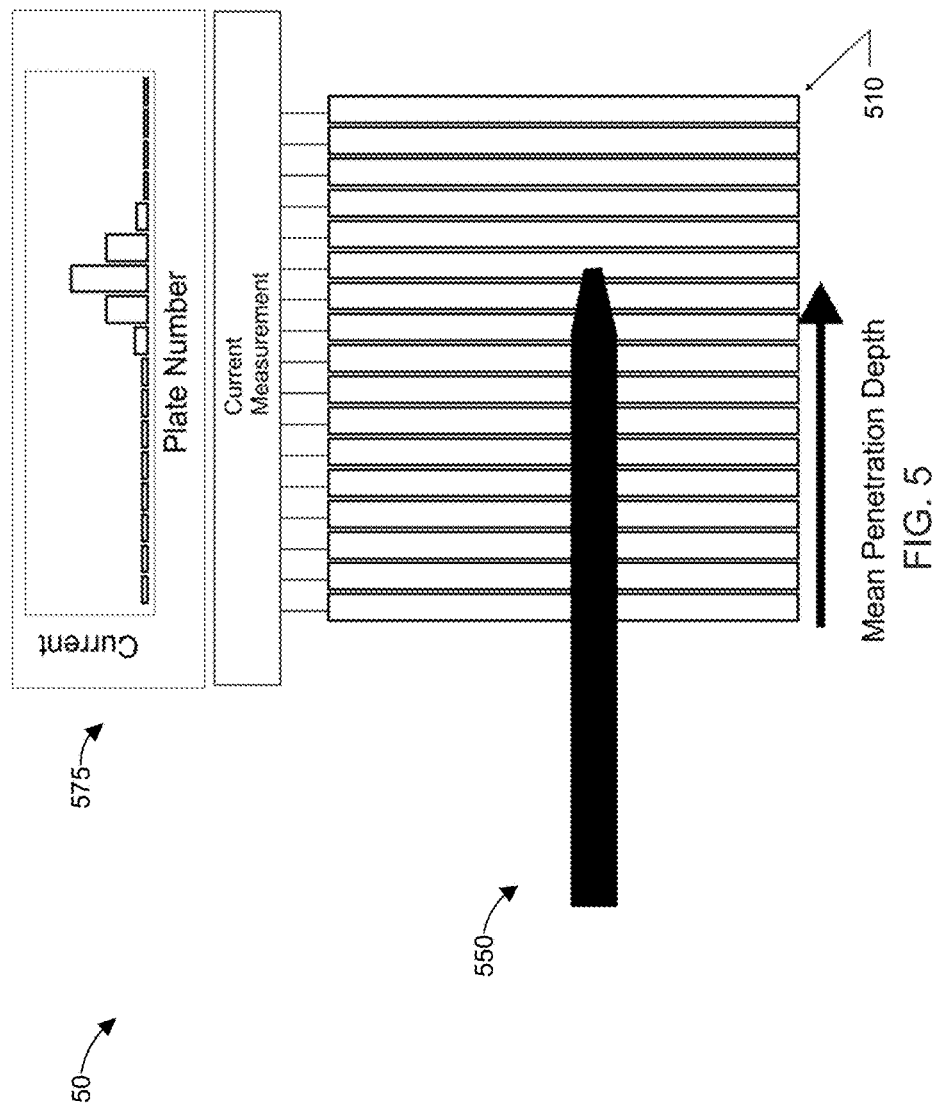
FIG. 5 is a diagrammatic view of an MLRV and its output according to one or more embodiments.

FIG. 5 is a diagrammatic view of a MLRV 50 and its output according to one or more embodiments. As discussed, an incident charged particle beam 550 (e.g., a pencil beam) is directed at MLRV 50. The metal plates 510 are oriented orthogonally to the direction of beam 550. For clarity, the insulator layers are not illustrated in FIG. 5.

As each charged particle from beam 550 passes through metal plates 510, it gradually loses energy and stops, depositing its single charge in that plate 510n. It is in the nature of ions that they tend to stop at a well-defined depth (i.e., plate number), forming a well-characterized and peaked depth distribution for a large number of charged particles of equal energy. The depth of peak (or centroid) of the distribution corresponds to the range of the particle in the metal plate 510 material, for the incident energy of beam 550. The device is also responsive to charge carriers that stop in the insulating layers. In such cases the charge is fixed in position but induces image charges in the adjacent conducting plates, thus the charge in the insulator produces a signal that is apportioned according to its relative distance from the two adjacent plates. The location (e.g., plate number) at which the particles from beam 550 stop is a function of the initial beam energy, and the mass and area density of each metal plate 510 and insulator layer.

The charge deposited on plate 510n by each charged particle causes a small current to form, which is detected by MLRV 50. An example of the output of MLRV 50 is illustrated in graph 575, which plots the detected current versus plate number at which the current was detected. The detected current level at a given metal plate 410n is directly proportional to the number of charged particles that stopped at that plate 510n. Thus, the detected current distribution has the same shape as the range distribution of beam 550 in the metal plate 510 material. An analysis of the current distribution yields information about the incident beam 550, including mean beam energy, any non-zero energy spread, and total incident current.

As discussed, the range of the charged particle is determined with respect to the metal plate 510 material. For example, a 250 MeV proton would normally traverse about 68 mm of pure copper, assuming its accepted density of 8.94 gm/cm$^3$. Note that if the density of the material was halved to 4.4 gm/cm$^3$, the range in millimeters would double to 136 mm. Thus, it is conventional to express the range in a form that is independent of the density of the material. This same range can be expressed as 59.84 gm/cm$^2$, which is the range multiplied by the corresponding material density. This unit is generally referred to in the art as the Area Density.

To model the range of a particle in the metal plate 510 material at different beam energies, it is useful to characterize each plate 510n in terms of its area density. For a plate of uniform thickness and density, the area density can be determined by measuring the total mass m and the total plate area A. The area density is simply m/A. For this reason, the mass and dimensions of each plate are determined which are measured at a high degree of precision prior to assembly, as discussed above.

Figure 6:
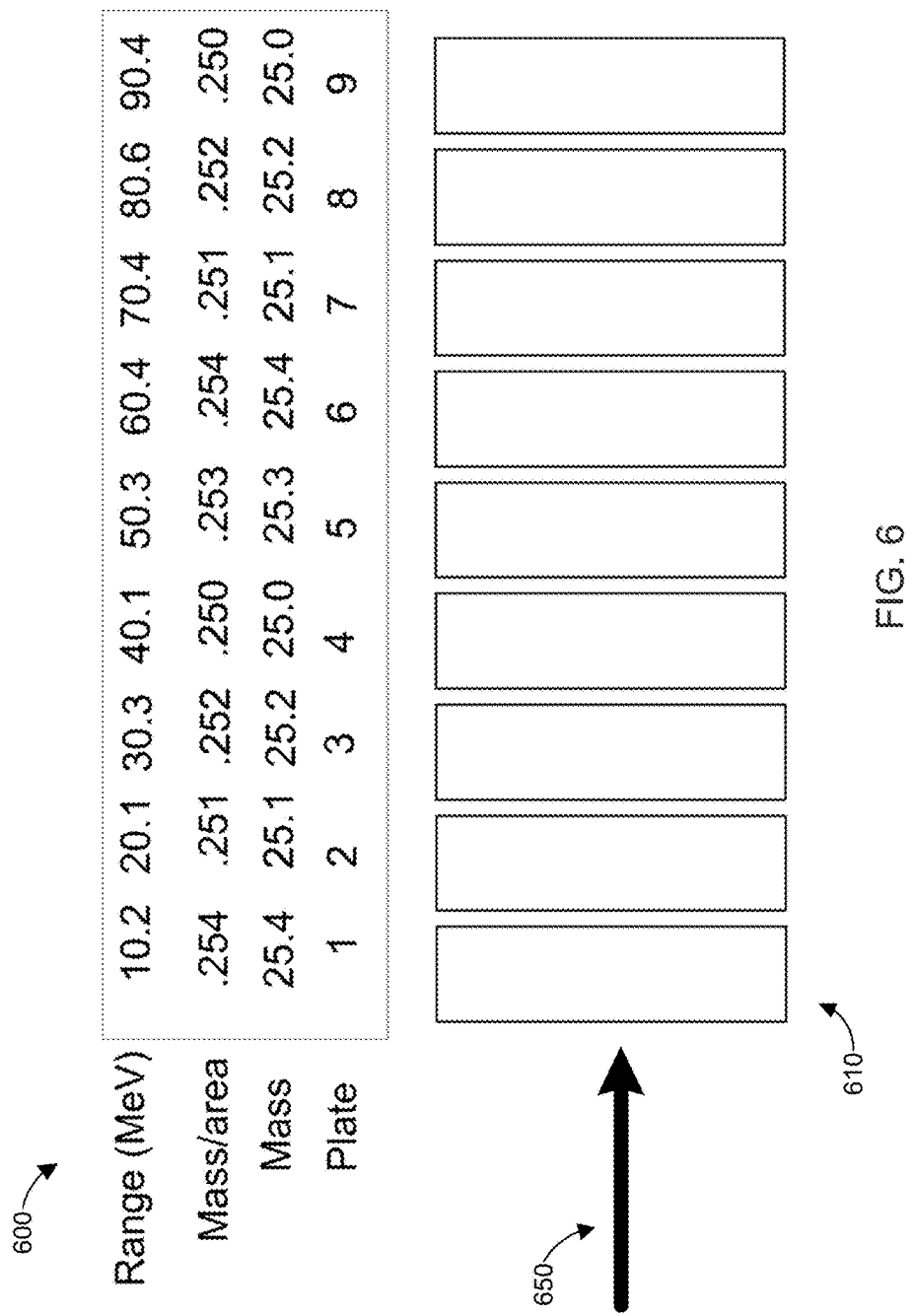
FIG. 6 illustrates a plurality of metal plates of a MLRV and an example table of characterization data and the theoretical mean range for each plate of a proton from an incident charged particle beam.

Given the measured values of area density for each plate and insulator, tables which relate beam energy to the mean range in plate material can be generated based on theoretical considerations. Alternately, the use of sophisticated physics modeling algorithms can generate a detailed prediction of charge distribution, which includes other effects such as the statistical spread in the primary peak, and elastic and inelastic nuclear scattering. The measured area density of the individual plates can be directly entered into the theoretical model, which will then generate the expected depth profile for an incident beam of arbitrary energy. This data can then be used to derive the actual beam energy spectrum from the current/depth data FIG. 6 illustrates a plurality of metal plates 610 of a MLRV and table 600 of characterization data and the theoretical mean range for each plate of a proton from an incident charged particle beam 650. The table 600 includes the mass/surface area (area density), mass, and plate number of each plate 610, which are used to model the beam 650 in the MLRV. For illustration purposes, the total area of each plate is 100 units. As shown in table 600, the mean range varies with the area density of each plate 610.

To increase the energy resolution sensitivity of an MLRV, a greater number of metal plates can be used. With plates having approximately equal total areas and purity, the energy resolution can be increased by using greater number of thinner, lower mass plates. For example, the MLRV can have 64 plates, 128 plates, 256 plates, or any value or range therebetween. The thickness of the plates can also be adjusted upwards or downwards to form a MLRV configured to detect particles having a high mean range or a low mean range, respectively. An important consideration in the selection of plate thickness is that lower-energy beams have a narrower depth distribution, and the accuracy of the method degrades if the plate thickness is comparable or greater that the peak width. An optimized apparatus can combine thinner plates at the detector entrance with thicker plates in the remainder of the stack to optimize energy resolution without increasing the number of plates.

Figure 7:
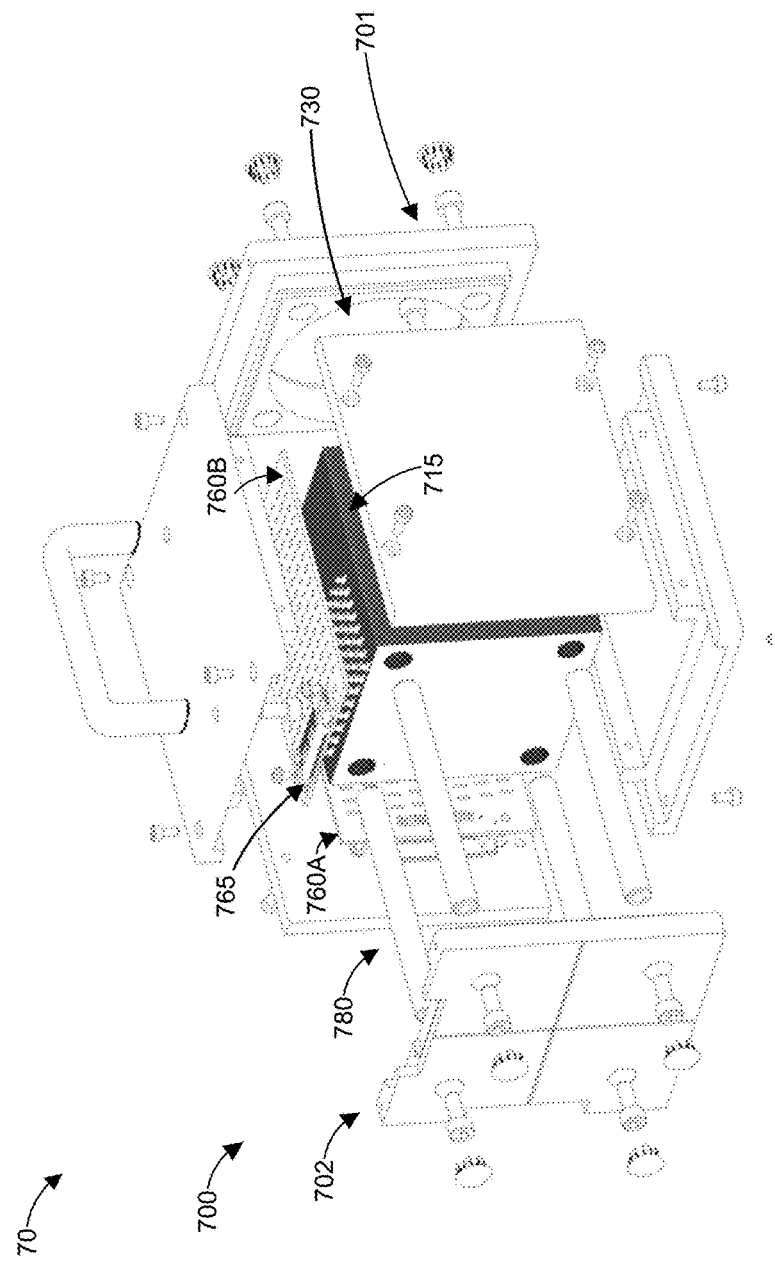
FIG. 7 is an expanded view of an MLRV assembly according to one or more embodiments.

FIG. 7 is an expanded view of an MLRV assembly 70 according to one or more embodiments. The assembly 70 includes four alignment rods 780 that extend through respective alignment holes of the metal plates and insulator layers as described above. The metal plates and insulator layers are oriented to face the front 701 of the housing 700, which includes an entry window 730 through which the charged particle beam passes. The alignment rods 780 are secured to opposing the front 701 and back 702 sides of the housing 700. Two circuit boards 760A, 760B are disposed on respective sides of the metal plate/insulator stack 715, between the housing 700 and the metal plate/insulator stack 715. Each circuit board 760 is electrically connected to a portion (e.g., half) of the metal plates in the metal plate/insulator stack 715 through electrical connection tabs as described above. An input/output port 765 of each circuit board 715 is externally accessible through housing 700. The port 765 can be a standard connection port as known in the art to interface with an external device, such as a current measurement array.

Figure 8:
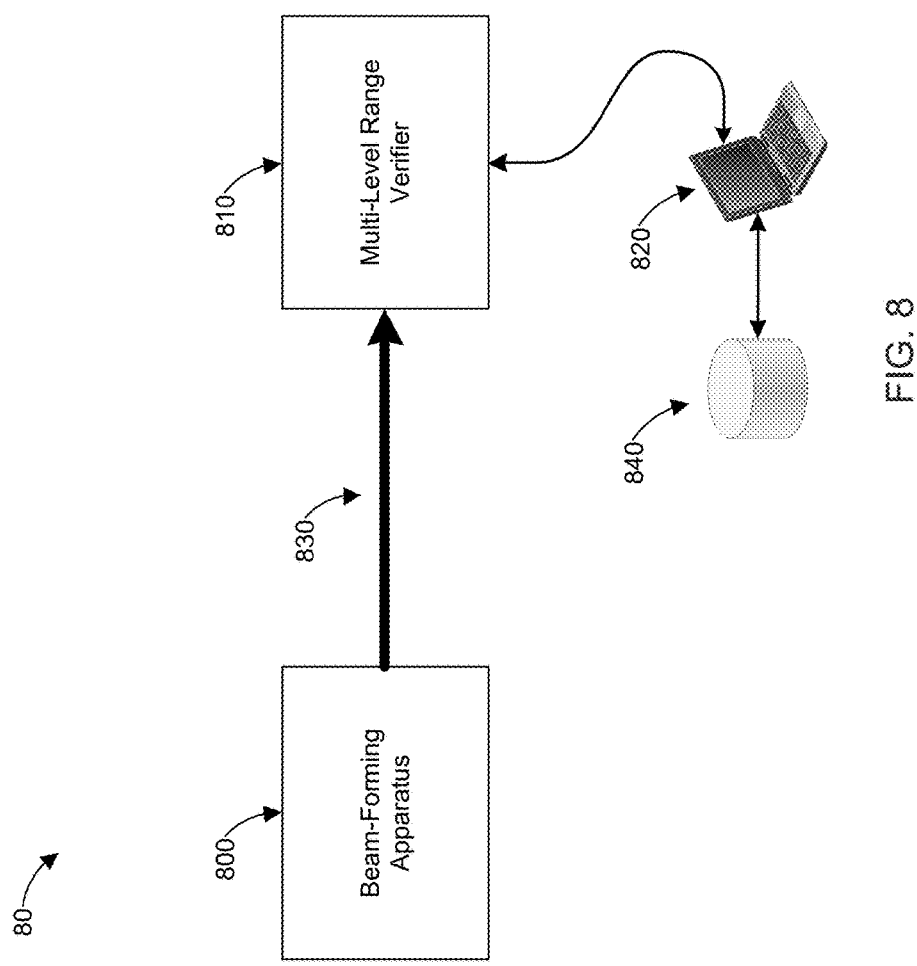
FIG. 8 is a block diagram of a system for verifying the range of a charged particle beam according to one or more embodiments.

FIG. 8 is a block diagram of a system 80 for verifying the range of a charged particle beam according to one or more embodiments. The system 80 includes a beam-forming apparatus 800, a multi-level range verifier 810, and a computer 820. The beam-forming apparatus 800 generates a charged particle beam 830 and directs the beam towards MLRV 810. The beam-forming apparatus 800 includes a beam source configured to generate the beam at a target energy level and one or more electromagnets to trim and/or deflect the beam 830. The beam 830 passes into MLRV 810 where each ion deposits its charge on a given metal plate, resulting in a current. The detected current from each plate is output form the MLRV 810 to the computer 820 for analysis. It is important to note that, although a single proton will stop in a single plate, a beam of many protons will stop in a range of depths due to the statistics of the stopping process. This forms a peak of some width. The width will vary with energy, being wider for higher energies. The detection of a multichannel peak is advantageous, since such data can be fit to a model with high accuracy.

First, the computer 820 characterizes the detected current distribution by determining its peak, median, and mean values. The computer 820 can perform additional statistical analysis of the detected current distribution as desired. For example, the computer 820 can determine the peak width, which is a convolution of the natural longitudinal range straggling and the actual energy spread of the beam 830. A Monte-Carlo calculation with a mono-energetic beam can be used to provide the longitudinal straggling. Then, the energy spread in the measured data can be extracted by assuming it is uncorrelated and adds in quadrature.

Next, the computer 820 compares the detected current distribution with a theoretical model of the energy distribution of a hypothetical beam passing through a hypothetical MLRV that contains metal plates that are formed out of the same material (e.g., copper) and with the same component area densities as MLRV apparatus 810. Through this comparison, the actual energy distribution and range of beam 830 can be determined with reasonable accuracy. For example, the model can incorporate each metal plate's area density and mass, along with its position (plate number) in MLRV apparatus 810. The area density of the insulators is also included in the model. The modeling can use the Monte-Carlo algorithm and an exact reproduction of the measured geometry (specifically the longitudinal geometry) derived from the area density and weight measurements of the plates and insulators. The software can launch a large number of simulated protons or other ions of defined energy and spatial distribution into the geometry. Each particle history is followed until the particle and all secondary particles and subsequent that it creates come to rest or escape. The resulting counts of charges in the various elements (conducting layers, insulating layers) are combined to produce the model spectrum. In particular, charged particles stopping in insulating materials are assumed to divide their charge between the adjacent conducting layers as described above. It is sufficient to divide the induced charges 50:50 between the adjacent conducting layers because the large number of particle histories generally leads to this division on average. Examples of Monte Carlo software than can perform these calculations are GEANT4 and FLUKA.

The MLRV 810 can provide an independent ab-initio measurement of an unknown beam energy based only on knowledge of the material stopping power used by the Monte-Carlo software and knowledge of the exact geometry.

A calibration between particle range in water (80% distal edge definition) and the peak centroid in MLRV 810 can be established either by experimental measurement or by software simulation. Range in water is the parameter of direct clinical interest. Subsequently the MLRV 810 can be used as an indirect means of measuring range in water that is far more convenient and stable than actual depth dose measurement using diagnostic water tank devices.

The measured data can be stored in a data file that is specific to the unique MLRV apparatus 810, which can be uniquely identified by serial number, bar code, or other unique identifier. The data file can be stored in a local or remote database 840, on a removable storage medium (e.g., disk, USB drive, CD, etc.), or in the internal memory of the computer 820.

The computer 820 maintains (locally or remotely) a table or database of the energy distribution and range measurements, as well as the date of each measurement. After each measurement, the computer 820 can statistically analyze this data to determine if the beam 830 characteristics have drifted or changed to a statistically significant degree since the last beam calibration. If so, the beam-forming apparatus 800 is recalibrated for at least the beam energy level that appears to have drifted or changed. Additional beam energy levels can also be recalibrated at this time. After recalibration, new verification measurements are taken with MLRV apparatus 810 at the calibrated energy level(s) and saved in the table/database. Future MLRV measurements will then be compared with the new verification measurements and those taken thereafter for a given beam 830 energy. The computer 820 can also determine statistically if the beam 830 characteristics have drifted over multiple energy levels, which may imply a systemic error that may not be detectable at a single energy level.

Figure 9:
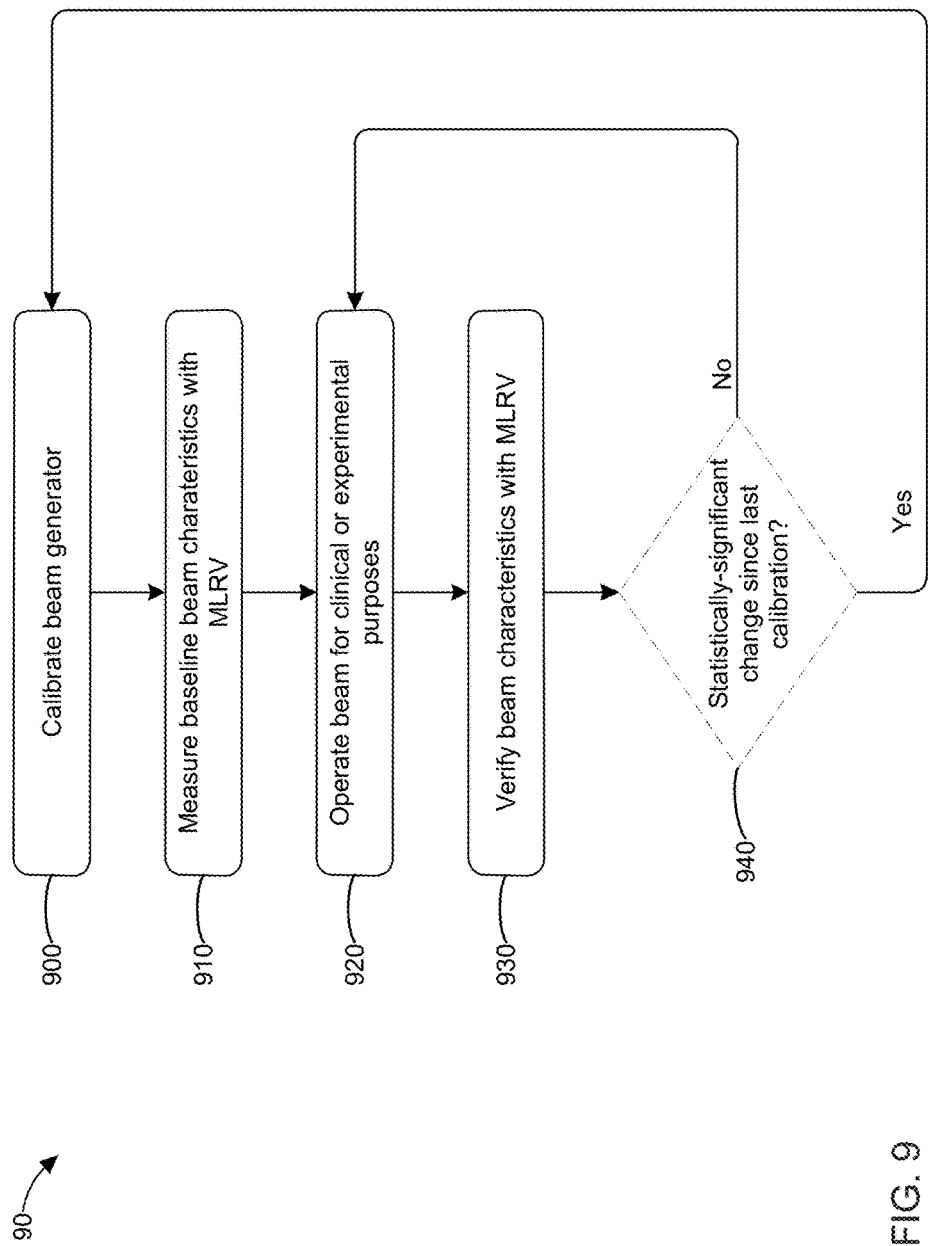
FIG. 9 is a flow chart of a method for determining whether a charged particle beam generator has fallen out of calibration according to one or more embodiments.

FIG. 9 is a flow chart 90 of a method for determining whether a charged particle beam generator has fallen out of calibration according to one or more embodiments. In step 900, the beam generator is calibrated at one or more energy levels. The calibration can be performed by taking measurements with an ion chamber in a water tank, as described above. In step 910, the calibrated beam is measured with an MLRV to generate a baseline characterization of the calibrated beam for each energy level that was calibrated in step 900. The characterization can include determining the energy distribution and range of the ions in the MLRV, as discussed above. In step 920, the beam generator is operated for clinical and/or experimental use for a predetermined time period in step 910. The predetermined time period can be one or more days, a week, several weeks, or a month. At the end of the time period, the beam characteristics are verified with the MLRV in step 930. The MLRV used in step 930 is preferably the same MLRV used in step 910, though this is not a requirement.

In step 940, the measured beam characteristics are statistically compared with the baseline beam characteristics to determine if there has been a material or clinically-significant change/drift in the beam characteristics since the last calibration. The value of a clinically-significant change is determined by the individual user or facility. If the measured beam characteristics differ from the baseline beam characteristics by a clinically-significant amount, which can be a threshold or minimum amount (e.g., at least 1% deviation from baseline), the beam generator is recalibrated (returning to step 900) and the method is repeated. If the measured beam characteristics do not differ from the baseline beam characteristics by a clinically-significant amount, the beam generator can continue clinical/experimental operation (returning to step 920) until the next predetermined time period at which point the beam characteristics are measured again with the MLRV in step 930. In next iteration through step 940, the statistical analysis can incorporate both the baseline beam characteristics, the prior measured beam characteristics, and the newly-measured measured beam characteristics. Alternatively, only the baseline beam characteristics and the newly-measured measured beam characteristics.

Some applications require measurement or comparison of proton beam energy at energies lower than about 100 MeV. A device with nominally uniform layer stopping power that can measure up to a typical maximum energy of 250 MeV with a reasonable number of layers, such as 128, suffers a degradation of energy resolution at lower energies. This can occur because the signal may be confined to a single channel, so that a calculation of the mean value of the peak positions lacks accuracy. To overcome this, plate thickness (and thus stopping power) can be reduced in the layers at the entrance end of the device. This adds some complication to the calibration of the device and can also compromise accuracy because the relative variation in thickness becomes larger.

To restore accuracy at lower energies, lower stopping power materials, such as aluminum or carbon, can be used instead of copper. Alternatively, a plastic which has been plated on one or both sides with a thin copper coating gives the same result in a convenient form which is readily obtained. An example is FR4-based PCB material plated with 0.25 oz/ft$^2$ copper on one or both sides. The density (1.4 g/cm$^2$) of this material is much less than that of solid copper. The fact that the material is not conductive in bulk does not affect the measurement as taught by Gottschalk and confirmed in experimental measurements.

Even with these measures for a beam with little energy spread, there will always be a low energy limit where the beam stops in only one or two plates, making it impossible to determine the centroid with high accuracy. Paradoxically, it is advantageous to have some energy spread in this circumstance. It is possible to artificially introduce a small, known energy spread into the beam. This allows the low-energy peaks in the distribution to be spread over at least two channels in a controlled manner while having an almost negligible effect on the high-energy peaks which are inherently broad. The energy spread can be produced using a plate with patterning across its area that produces a stopping power and thus degradation of the beam energy that differs from point to point with a spatial distribution small compared to the lateral dimensions of the beam at the beginning of the stack of layers. This may be achieved for example by machining closely spaced ridges into a plate to form a micro-ridge filter. This is somewhat analogous to the use of so-called "Ridge Filters" in particle therapy for creating a longitudinally spread-out dose distribution in the patient from a single-energy initial beam by changing it to a beam with a range of energies. The micro-ridge filter may be integrated into the insulating housing or it may be an externally-applied accessory. It is preferably placed before the primary stack.

Figure 10:
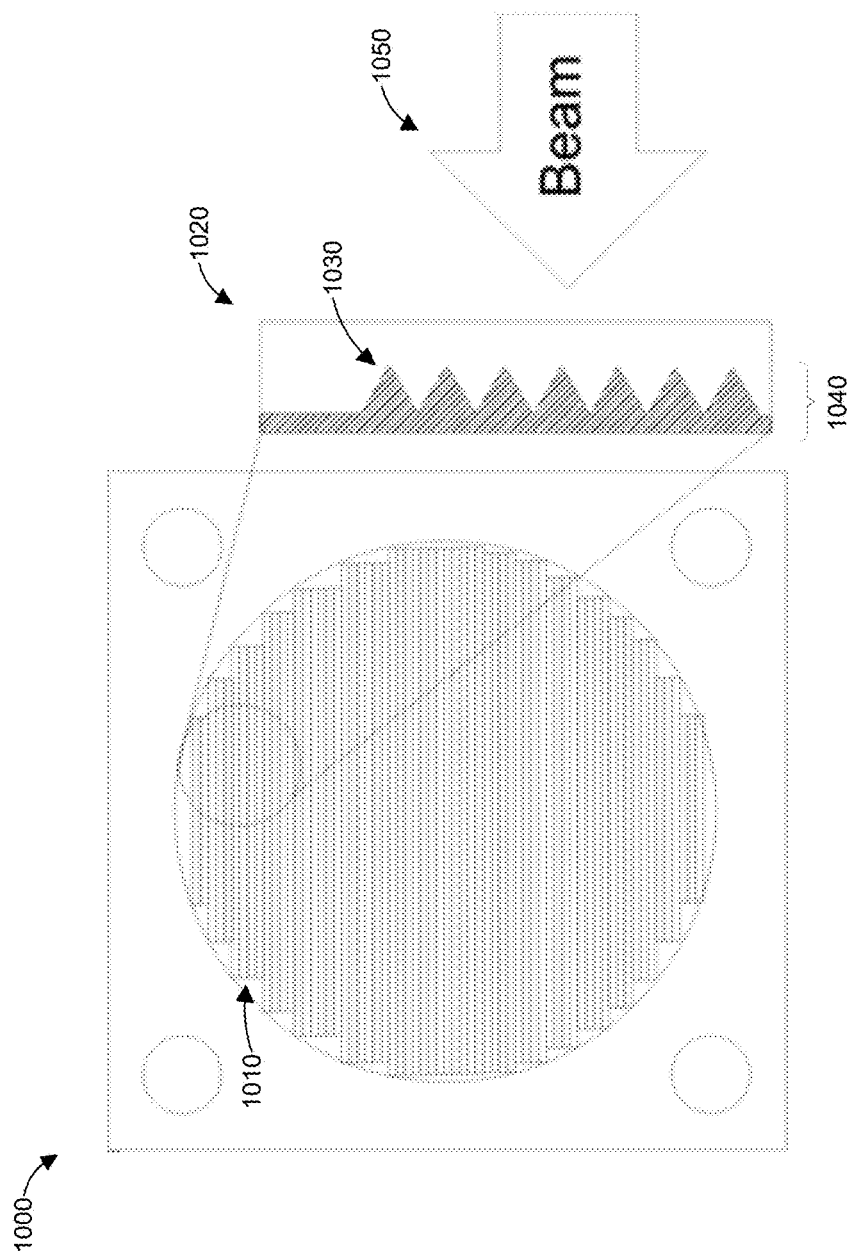
FIG. 10 illustrates a micro-ridge filter according to an embodiment.

FIG. 10 illustrates a micro-ridge filter 1000 according to an embodiment. The filter can be constructed from a low-density insulating material, or copper or similar metal, but would most typically match the construction material used in the primary plate stack. The filter 1000 includes a plurality of rows 1010 of ridges across the face of the filter 1000. The rows 1010 are parallel to one another, though this is not a requirement. As illustrated in zoomed-in view 1020, the ridges 1030 result in a varied thickness 1040 of similar to a saw-tooth pattern, along the vertical direction, which is orthogonal to the direction of travel of beam 1050. A maximum thickness 1040 of material equivalent to two standard layers of the MLRF will introduce a range shift of one layer of thickness, and thus a range variation of +/−1 standard MLRF layer. This guarantees a range distribution of at least three plates at any energy down to the minimum energy limit of the MLRF. Because the range spread due to this introduced energy spread adds in quadrature to the spread due to statistical range straggling, it would not have a large effect at higher energies, which already have a substantial range spread. Since the ridge filter is well-characterized, its effect of range and energy spread can be accurately modeled, and compensated for when calculating beam mean energy and energy spread. It can also be made simply and can be removable for measurements made at higher energy. In an alternative embodiment, micro-ridge filter 1000 can have ridges in a grid pattern.

Figure 11:
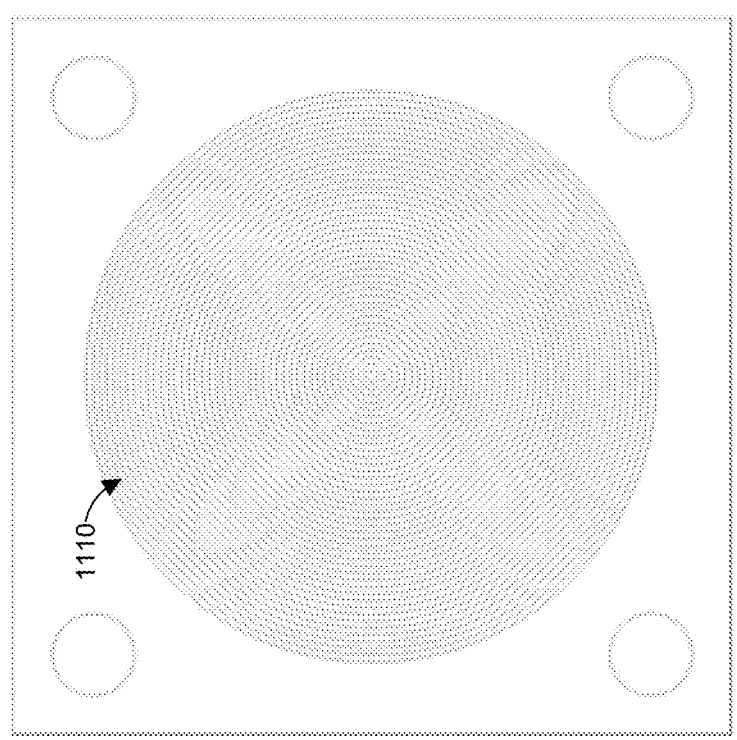
FIG. 11 illustrates a micro-ridge filter according to another embodiment.

FIG. 11 illustrates a micro-ridge filter 1100 according to another embodiment. The micro-ridge filter 1100 includes a plurality of concentric circles 1110 of ridges. A zoomed-in view of micro-ridge filter 1100 would also illustrate a saw-tooth pattern as in zoomed-in view 1020 of micro-ridge filter 1000. In an alternative embodiment, micro-ridge filter 1100 can have ridges in a spiral pattern.

As can now be appreciated, the present disclosure provides improved systems and methods for verifying the calibration of a charged particle pencil beam. The system includes an EMI-shielded housing having a plurality of conductive plates and insulation layers. The conductive plates are formed out of a material, such as copper, having a high purity level such that its composition is substantially uniform and known to a high degree of certainty. Each plate's surface area and mass is known to a high degree of accuracy. In addition, each plate's location in the system is known. The charged particles in the incident beam cause a current to form in the plate in which each particle stops, resulting in a current distribution. The measured current distribution can be compared with a model that uses each plate's composition to characterize the beam's baseline range and energy distribution after the beam is calibrated.

After the beam has been used for a certain time period, for example for therapeutic or experimental purposes, the system can be used to verify the beam's range and energy distribution by comparing a verification current distribution with the model. If the verified beam range and/or the verified energy distribution differs from the baseline range and/or the baseline energy distribution in a statistically significant manner, the beam can be recalibrated. Therefore, the systems and methods disclosed herein provide a convenient and accurate means to verify the calibration of a charged particle beam.

The present invention should not be considered limited to the particular embodiments described above, but rather should be understood to cover all aspects of the invention as fairly set out in the present claims. Various modifications, equivalent processes, as well as numerous structures to which the present invention may be applicable, will be readily apparent to those skilled in the art to which the present invention is directed upon review of the present disclosure. The claims are intended to cover such modifications.

What is claimed is:
1. A kit comprising:
an apparatus comprising:
an electrically-conductive housing;
an entry window defined in the housing, the entry window comprised of a radiation-resistant polymer material, the entry window having an interior surface facing an interior of said housing and an exterior surface facing away from said housing;
a conductive film disposed on said interior surface of said window and at least a portion of an interior surface of said housing proximal to said window, such that the conductive film and the housing in combination forms a continuous electrically-conductive shield;
a plurality of metal plates disposed in said housing, each metal plate having an electrical contact tab extending from at least one common edge of said metal plate, each said metal plate having opposing first and second metal faces, each plate having a known composition, each plate oriented so that said first and second metal faces are parallel to said entry window;
a plurality of insulator films disposed in said housing, each insulator film disposed between adjacent metal plates, each insulator sized to cover said first or said second face of said adjacent metal plates; and
a printed circuit board disposed in said housing, said circuit board in electrical contact with at a first subset of the electric contact tabs on said plurality of metal plates; and
a non-transitory computer-readable medium comprising data representing:
a position of each metal plate in said housing;
a mass of each metal plate; and
an area density of each metal plate.
2. The kit of claim 1, wherein the data on said non-transitory computer-readable medium includes the known composition of each metal plate.
3. The kit of claim 1, wherein said metal plates comprise copper of at least 99% purity.
4. The kit of claim 1, wherein said housing is formed of aluminum.
5. The kit of claim 1, wherein said conductive film includes at least one of nickel or gold.
6. The kit of claim 5, wherein said conductive film comprises a first layer of nickel and a second layer of gold, said second layer disposed on said first layer.
7. The kit of claim 1, wherein the window comprises a polyimide film.
8. The kit of claim 1, wherein each metal plate has approximately a same mass, wherein approximately means less than or equal to a one percent variation from a mean mass of said plurality of plates.
9. The kit of claim 1, wherein each metal plate has alignment holes defined in a common location of said plates.
10. The kit of claim 9, further comprising alignment rods disposed through said alignment holes.
11. The kit of claim 1, further comprising a second circuit board disposed in said housing, said second circuit board in electrical contact with a second subset of the electric contact tabs on said plurality of metal plates, the second subset of electrical tabs extending from a second common edge of said metal plates.

\* \* \* \* \*